Feb. 12, 1974 F. W. ANDERSON Plant Pat. 3,478
NECTARINE TREE
Filed Oct. 13 1972
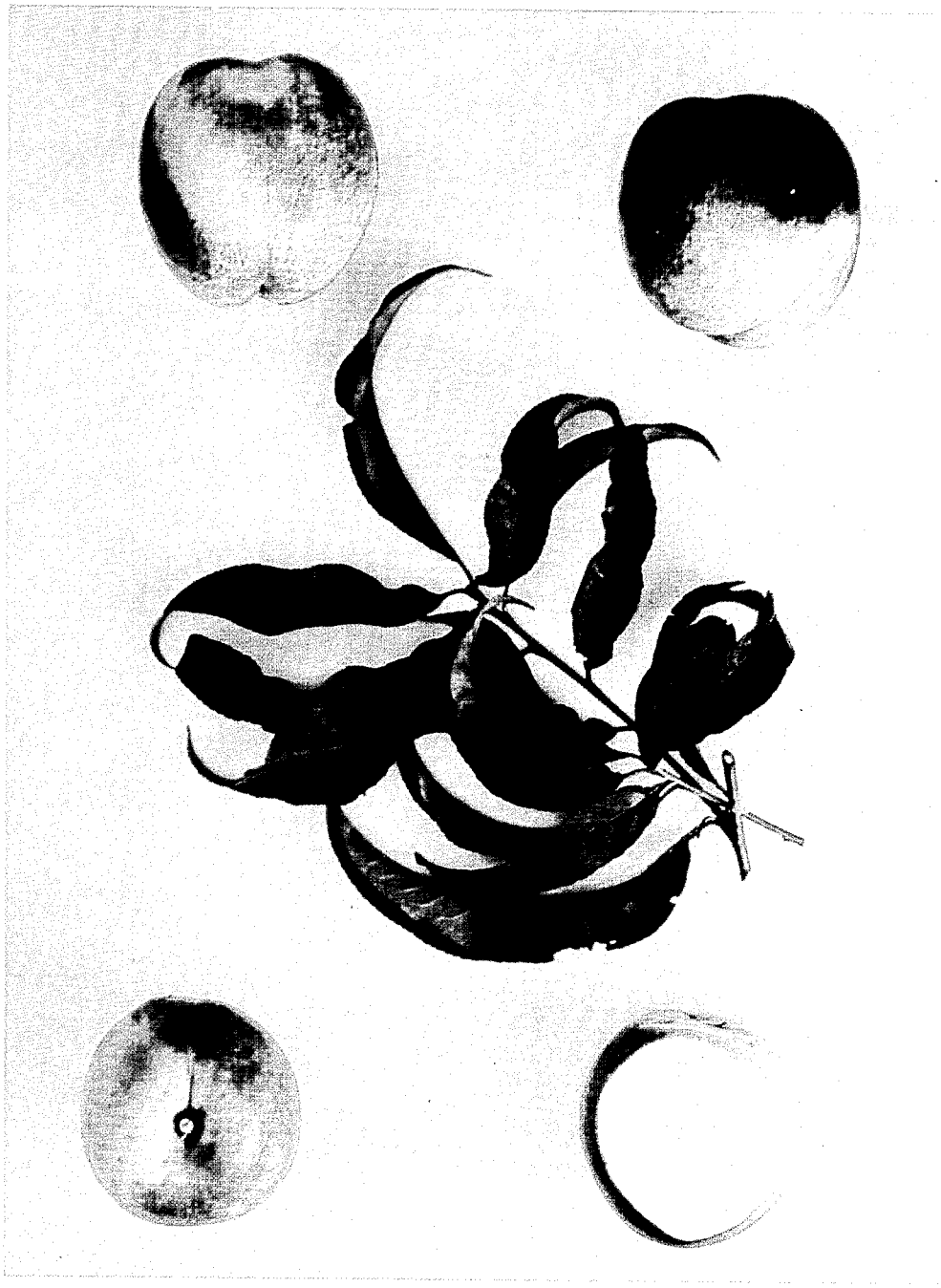

United States Patent Office

Plant Pat. 3,478
Patented Feb. 12, 1974

3,478
NECTARINE TREE

Frederic W. Anderson, Merced, Calif., assignor to
Reedley Nursery, Inc., Reedley, Calif.

Filed Oct. 13, 1972, Ser. No. 297,378
Int. Cl. A01h 5/03
U.S. Cl. Plt.—41 1 Claim

ABSTRACT OF THE DISCLOSURE

A nectarine tree which is large, vigorous, upright to spreading, open, vase-formed, foliated with large lanceolate, acutely pointed leaves having a crenate margin and reniform glands, and a regular and productive bearer of large to medium size, uniform, symmetrical, globose, clingstone fruit having smooth, lemon-yellow skin substantially overspread with red shading to a deeper purple-red, yellow flesh, and a red pit cavity with the red streaked into the flesh.

Background of the variety: Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

Origin of the variety: The present variety of nectarine tree was originated by me, in my experimental nursery and orchard located as aforesaid, as a first generation ($F_1$) cross between the Late Le Grand nectarine (U.S. Plant Pat. No. 1,035) as the seed parent, and an unamed nectarine seedling (unpatented) as the pollen parent—the latter having a very smooth skin, but failing to ripen in the Central Valley of California. In maturity, such cross evidenced certain novel and distinctive characteristics desirable for a commercially grown nectarine, and I, therefore, undertook asexual reproduction of its preparatory to introduction to the trade.

Asexual reproduction of the variety: I asexually reproduced the present variety of nectarine tree by top-working the same on mature orchard trees located in my said experiimental orchard, and such reproductions were found to run true to the original tree in all respects.

Summary of the variety: The present variety of nectarine tree is large, vigorous, upright to spreading, open, vase-formed, foliated with large, lanceolate, acutely pointed leaves having a crenate margin and reniform glands, and a regular and productive bearer of large to medium size, uniform, symmetrical, globose, clingstone fruit having smooth, lemon-yellow skin substantially overspread with red shading to a deeper purple-red, yellow flesh, and a red pit cavity with the red streaked into the flesh.

The present variety of nectarine tree is also characterized, in particular comparison to the Regal Grand (U.S. Plant Pat. No. 1,751) and the September Grand (U.S. Plant Pat. No. 1,755) nectarines, as follows:

The fruit of the present variety is somewhat similar to the Regal Grand, but ripens about two weeks later and approximately with the September Grand, and—in further comparison to the latter—is smaller, but more uniform in size, smoother, of a deeper, more attractive red color, and does not crack during humid conditions existing at the ripening period.

Brief description of the drawing: The drawing is an illustration, by photographic reproduction in color, of leaves and fruit of the variety; one fruit being partiallly cut away to expose the flesh.

Description of the variety: The botanical details of this new and distinct variety of nectarine tree—with color definitions (except those in common color terms) referenced to Maerz and Paul Dictionary of Color—are as follows:

Tree:
- *Size.*—Large.
- *Vigor.*—Vigorous.
- *Growth.*—Upright to spreading.
- *Density.*—Open.
- *Form.*—Vase-formed.
- *Productivity.*—Productive.
- *Bearing.*—Regular bearer.

Trunk:
- *Size.*—Medium.
- *Texture.*—Medium.

Branches:
- *Size.*—Medium.
- *Texture.*—Medium.

Leaves:
- *Size.*—Large. Average length—6". Average width—1¼".
- *Form.*—Lanceolate. Acute pointed.
- *Thickness.*—Medium.
- *Texture.*—Smooth.
- *Margin.*—Crenate.
- *Petiole.*—Medium length, medium thickness.
- *Glands.*—Average number—3. Alternate, medium size, reniform. Usually positioned 2 on petiole, and 1 or 2 on blade.
- *Color.*—Top side—medium green (23–J–6). Under side—Lighter green (21–I–6).

Flower buds:
- *Size.*—Medium.
- *Length.*—Medium.

Flowers:
- *Blooming period.*—Medium, as compared with other varieties.
- *Size.*—Large.
- *Color.*—Pink.

Fruit:
- *Maturity when described.*—Eating ripe—Aug. 24, 1972.
- *Date of first picking.*—Aug. 15, 1972.
- *Date of last picking.*—Aug. 25, 1972.
- *Size.*—uniform, medium to large. Average diameter axially—2⅝". Average transversely in suture plane—2⅝".
- *Form.*—Uniform, symmetrical, globose.
- *Suture.*—Shallow. Extends from base to beyond apex. Marked depression beyond pistil point.
- *Ventral surface.*—Rounded strongly.
- *Lips.*—Equal to unequal.
- *Cavity.*—Elongated in suture plane, with suture showing on both sides.
- *Base.*—Truncate.
- *Apex.*—Very short, depressed.

Skin:
- *Thickness.*—Medium.
- *Texture.*—Medium.
- *Tenacity.*—Tenacious to flesh.
- *Tendency to crack.*—None.
- *Down.*—Wanting.
- *Color.*—Lemon-yellow (9–L–2) substantially overspread with red (6–L–5) shading darker to purple-red (48–L–1).

Flesh:
- *Texture.*—Firm, crisp, meaty.
- *Fibers.*—Fine.
- *Ripens.*—Evenly.
- *Flavor.*—Subacid.
- *Aroma.*—Distinct.
- *Eating quality.*—Good.
- *Color.*—Yellow (9–L–4).

*Surface of pit cavity.*—Red (6–L–5), with the red streaked into the flesh.

Stone:

*Type.*—Cling.

*Size.*—Medium. Average length—1⅛". Average breadth—1". Average thickness—9/16".

*Form.*—Globose to oblong.

*Base.*—Straight.

*Apex.*—Rounded.

*Sides.*—Equal.

*Ridges.*—Rounded.

*Ventral edge.*—Thick.

*Dorsal edge.*—Full.

*Tendency to split.*—Slight.

*Color.*—Dark red (48–L–3).

Use: Market—local. Dessert. Long distance shipping.

Keeping quality: Good.

Resistance to insects and diseases: No unusual susceptibilities noted.

Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, which is larger, vigorous, upright to spreading, open, vase-formed, foliated with large, lanceolate, acutely pointed leaves having a crenate margin and reniform glands, and a regular and productive bearer of large to medium size, uniform, symmetrical, globose, clingstone fruit having smooth, lemon-yellow skin substantially overspread with red shading to a deeper purple-red, yellow flesh, and a red pit cavity with the red streaked into the flesh; the variety being further characterized by fruit which is somewhat similar to the Regal Grand but ripens about two weeks later and approximately with the September Grand, and—as to the latter—by fruit which is smaller but more uniform in size, smoother, of a deeper red color, and does not crack during humid conditions at the ripening period.

No references cited.

ROBERT E. BAGWILL, Primary Examiner